(12) United States Patent
Mori

(10) Patent No.: US 7,496,221 B2
(45) Date of Patent: Feb. 24, 2009

(54) RADIOLOGICAL IMAGE DIAGNOSTIC SYSTEM AND DATA PROCESSING METHOD THEREOF

(75) Inventor: Issei Mori, Sendai (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 376 days.

(21) Appl. No.: 11/072,535

(22) Filed: Mar. 7, 2005

(65) Prior Publication Data

US 2005/0201635 A1    Sep. 15, 2005

(30) Foreign Application Priority Data

Mar. 10, 2004  (JP) .............................. 2004-068027

(51) Int. Cl.
*G06K 9/00* (2006.01)
*G06K 9/40* (2006.01)

(52) U.S. Cl. ........................ 382/131; 382/254
(58) Field of Classification Search ....................... None
See application file for complete search history.

(56) References Cited

U.S. PATENT DOCUMENTS

2004/0247167 A1 * 12/2004 Bueno et al. ................ 382/132

FOREIGN PATENT DOCUMENTS

| JP | 53-126892 | 11/1978 |
|---|---|---|
| JP | 2002-119504 | 4/2002 |

OTHER PUBLICATIONS

T.M. Peters, et al., "Computed Tomography with Fan Beam Geometry", Journal of Computer Assisted Tomography, vol. 1, No. 4, 1977, pp. 429-436.

* cited by examiner

*Primary Examiner*—Bhavesh M Mehta
*Assistant Examiner*—Charles Kim
(74) *Attorney, Agent, or Firm*—Oblon, Spivak, McClelland, Maier & Neustadt, P.C.

(57) ABSTRACT

A radiological image diagnostic system is provided with a radiation generating unit, a radiation detecting unit, a clipping-correction unit and an image reconfiguration unit. The radiation generating unit generates a radiation. The radiation detecting unit detects the radiation from the radiation generating unit. The clipping-correction unit applies a clipping process to a radiation detected value by the radiation detecting unit and applies a mean value correction process to data acquired based upon the radiation detected value so that the separation of the local mean of the data acquired based upon the radiation detected value before and after the clipping process is reduced. The image reconfiguration unit generates an image using data acquired based upon a radiation detected value after the clipping process and after the mean value correction process.

7 Claims, 7 Drawing Sheets

RADIOLOGICAL IMAGE DIAGNOSTIC SYSTEM AND DATA PROCESSING METHOD THEREOF

CROSS REFERENCES TO RELATED APPLICATIONS

The present application relates to and incorporates by reference Japanese Patent application No. 2004-068027 filed on Mar. 10, 2004.

BACKGROUND OF THE INVENTION

1. Field of the Invention

The present invention relates to a radiological image diagnostic system that radiates a radiation such as X-rays on an examined body and visualizes the inside of the examined body and a data processing method thereby.

2. Description of the Related Art

Heretofore, a radiological image diagnostic system has been used for a system for photographing a tomographic image of the inside of an examined body. Its representative example is an X-ray CT system (for example, refer to a document, "Method for Suppressing Streak Artifacts in CT Resulting from Excessive Noise" on pp. 272 to 276 of Medical Imaging Technology, 21 (4), 2003 written by I. Mori and M. Kazama). In X-ray CT, X-rays are radiated on an examined body from an X-ray tube and the X-rays transmitted in the examined body are detected in an X-ray detector and a data acquisition system (DAS). Further, processing including a logarithmic transformation process is applied to an X-ray detected value by a detection system including the X-ray detector and DAS and projection data is acquired. The projection data is reconfigured and an X-ray CT image is generated.

However, in an ultralow dosage area of an X-ray detected value, there is a case that the number of detected X-ray photons is substantially zero and so-called clipping may occur.

The X-ray detected value will be described below. A digital signal output from DAS is the sum of a signal s proportional to the number of X-ray incident photons on the detector, an offset o when the number of X-ray incident photons is zero and noise n. Precisely, further, the sensitivity constant and others of the detector and DAS are also related, however, as they are not related to the object of the invention, they are omitted. A preparation unit is provided with a function for acquiring a value acquired by subtracting the offset o, that is, s+n. This processing is called offset processing or offset correction. "s+n" is the X-ray detected value. In the case of data acquired by further applying slight processing to the X-ray detected value acquired as a result of offset correction, it is also called an X-ray detected value in the invention if no logarithmic transformation is applied to the data.

As the noise n is a positive or negative indeterminate value, the X-ray detected value x may have a negative value in case the signal output s is sufficiently small in comparison with the noise n. In case the X-ray detected value x is a negative value, logarithmic transformation cannot be executed and logarithmic transformation itself has no physical meaning. In such a case, generally, the X-ray detected value x is clipped to be 1 which is the minimum value for processing of the X-ray detected value x in a radiological image diagnostic system.

FIG. 9 is an explanatory drawing for explaining the concept of clipping executed in case an X-ray detected value is in an ultralow dosage area.

In a graph shown in FIG. 9, an abscissa shows a data value on the input side of logarithmic transformation and an ordinate shows a data value on the output side of logarithmic transformation. A solid curve in the graph shows a logarithmic function D1. Further, distributional data in a direction of the abscissa is distributional data on the input side D2 of logarithmic transformation and distributional data in a direction of the ordinate is a distribution data D3 showing the output of the logarithmic transformation of the distributional data D2. That is, the distributional data D2 is equivalent to an X-ray detected value and the distributional data D3 is equivalent to projection data. Precisely, though D3 is not projection data and projection data is acquired by applying some processes to D3, D3 is regarded as projection data in the invention because the processes are not important in the invention and a problem of clipping in D3 is reflected in projection data.

In the distributional data D2, as logarithmic transformation cannot be applied to a part having a negative value in a part D2a having a value smaller than 1 and a value equal to or smaller than 1 even if it is zero is equal to or smaller than a minimum unit which the system can deal, these values are all raised to be 1. This raise is called clipping. Therefore, the distributional data D3 after logarithmic transformation is remarkably distorted and a mean value D4 of the distributional data D3 is raised from the logarithm D5 of the mean value of the distributional data D3. As a result of the clipping, a mean value of projection data is shifted from a true mean value to a lower value.

Generally, as a value of projection data is acquired by multiplying a scaling constant by the value of projection data after logarithmic transformation is applied to an X-ray detected value and inverting its sign, a mean value of projection data is underestimated under a condition in which clipping occurs in comparison with a mean value of projection data in case no noise is included. A component the value of which is larger of projection data means that larger X-ray attenuation occurs and a component the value of which is smaller of projection data means that smaller X-ray attenuation occurs. In an image acquired by a reconfiguration process using such projection data, a CT value of a part in which large X-ray attenuation occurs is shifted and shaded.

That is, as described above, a conventional type radiological image diagnostic system has a problem that the shift and shading of a CT value occur in an X-ray CT image by clipping and the problem is currently sufficiently avoided.

Therefore, the development of technique for avoiding the occurrence of the shift and shading of a CT value of an X-ray CT image by clipping even if an X-ray detected value is in an ultralow dosage area is expected.

SUMMARY OF THE INVENTION

The invention is made to cope with such a conventional situation and the object is to provide a radiological image diagnostic system and a data processing method of the system in which the occurrence of the shift and shading of a CT value of a radiological CT image by clipping even if a radiation detected value is in an ultralow dosage area can be reduced.

The radiological image diagnostic system according to the invention is provided with a radiation generating unit for generating a radiation so as to achieve the object, a radiation detecting unit for detecting the radiation from the radiation generating unit, a clipping-correction unit for applying a clipping process to a radiation detected value by the radiation detecting unit and applying a process for correcting a mean value to data acquired from the radiation detected value so that the separation of local means of data acquired based upon the radiation detected value before and after clipping is reduced and an image reconfiguration unit for generating an image using data acquired based upon the radiation detected value after the clipping process and after the process for correcting the mean value.

Besides, the radiological image diagnostic system according to the invention is provided with a radiation generating unit for generating a radiation, a radiation detecting unit for detecting the radiation from the radiation generating unit, a clipping unit for applying a clipping process to a radiation detected value by the radiation detecting unit, an output correction unit for applying a mean value maintenance correction process to the radiation detected value after the clipping process so that the separation of local means of the radiation detected values before and after clipping is reduced and a logarithmic transformation unit for generating projection data by applying a process including a logarithmic transformation process to the radiation detected value after the mean value maintenance correction process so as to achieve the object.

Besides, the radiological image diagnostic system according to the invention is provided with a radiation generating unit for generating a radiation, a radiation detecting unit for detecting the radiation from the radiation generating unit, a clipping unit for applying a clipping process to a radiation detected value from the radiation detecting unit, a logarithmic transformation unit for generating logarithmic transformation data by applying a logarithmic transformation process to the radiation detected value after clipping and a logarithmic transformation data correction unit for executing a mean value correction process for multiplying by a coefficient so that the local mean of the logarithmic transformation data approaches to a value generated by logarithmic transformation from the local mean of the radiation detected value before clipping so as to achieve the object.

Besides, a data processing method of the radiological image diagnostic system according to the invention is provided with a step for applying a clipping process to a radiation detected value and applying a mean value correction process to data acquired based upon the radiation detected value so that the separation of the local means of data acquired based upon the radiation detected value before and after clipping is reduced and a step for generating an image using data acquired based upon the radiation detected value after the clipping process and after the mean value correction process so as to achieve the object.

According to the above-mentioned radiological image diagnostic system and the data processing method of the system according to the invention, even if a radiation detected value is in an ultralow dosage area, the occurrence of the shift and shading of a CT value of a radiological CT image by clipping can be reduced.

DESCRIPTION OF THE PREFERRED EMBODIMENTS

Referring to the attached drawings, embodiments of a radiological image diagnostic system and a data processing method of the system according to the invention will be described below.

Figure 1:
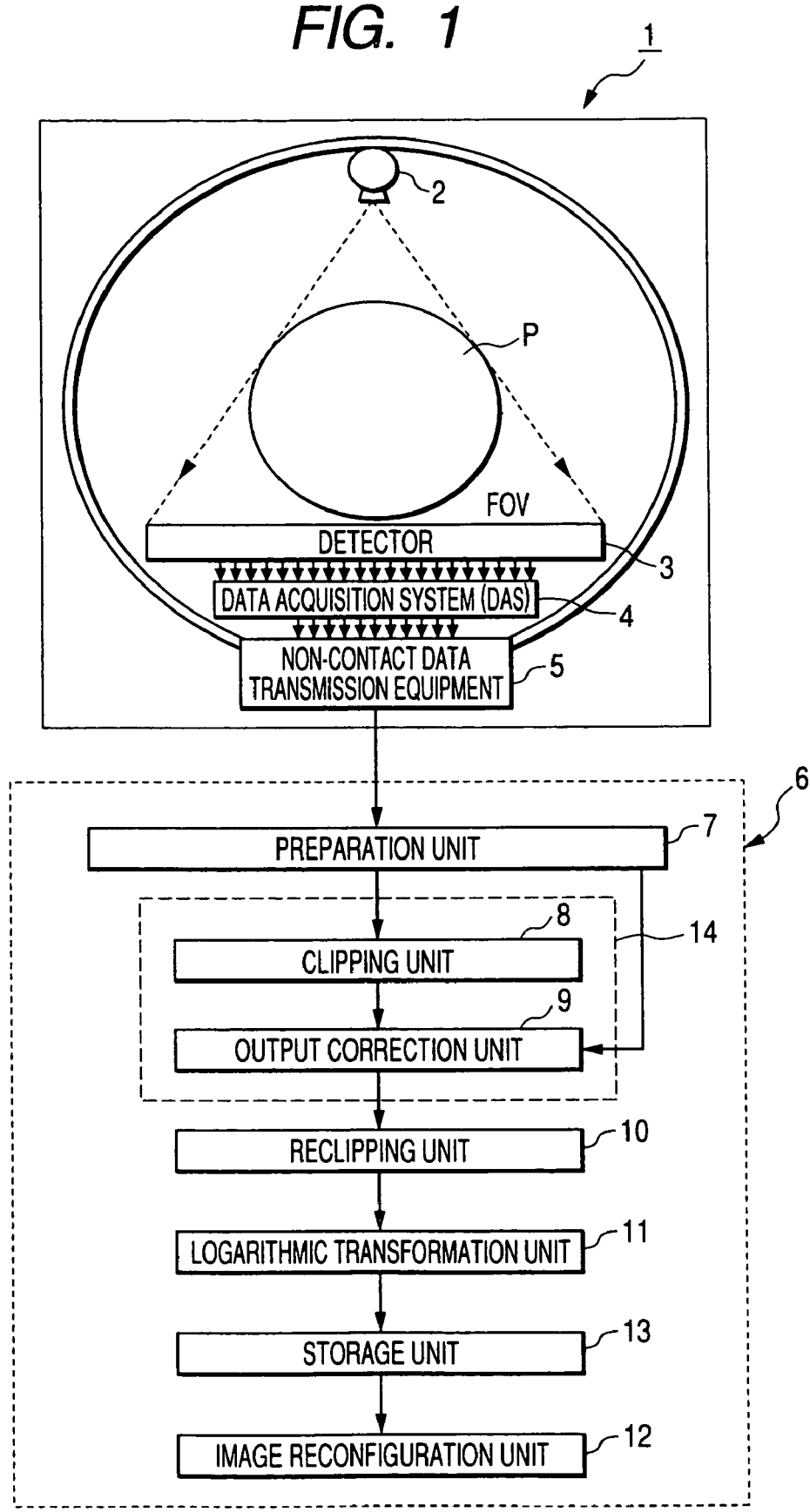
FIG. 1 is a block diagram showing a first embodiment of a radiological image diagnostic system according to the invention.

FIG. 1 is a block diagram showing a first embodiment of the radiological image diagnostic system according to the invention.

The radiological image diagnostic system 1 will be described below as an X-ray CT system, however, in principle, another radiological image diagnostic system such as a gamma-ray CT system is also possible.

The radiological image diagnostic system 1 is provided with an X-ray tube 2 as a radiation generating unit, an X-ray detector 3 as a radiation detecting unit and a data acquisition system (DAS) 4. DAS 4 is connected to a controller 6 via data transmission equipment 5.

The controller 6 is installed by reading a program in a computer or is realized by a predetermined circuit, functions as a preparation unit 7, a clipping unit 8, an output correction unit 9, a reclipping unit 10, a logarithmic transformation unit 11 and an image reconfiguration unit 12, and is further provided with a storage unit 13. A clipping-correction unit 14 is realized by the clipping unit 8 and the output correction unit 9.

Further, an examined body P is set between the X-ray tube 2 and the X-ray detector 3.

The X-ray tube 2 is connected to a high-voltage power source not shown and is arranged so that it can radiate X-rays which is a radiation on the examined body P.

The X-ray detector 3 is provided with a function for detecting the X-rays transmitted in the examined body P, converting it to an electric signal and sending the electric signal to DAS 4.

DAS 4 is provided with a function for converting the electric signal received from the X-ray detector 3 to a digital signal and sending the digital signal to the controller 6 via the data transmission equipment 5 as an X-ray detected value.

The preparation unit 7 is provided with a function for receiving the X-ray detected value from DAS 4 via the data transmission equipment 5 and sending the X-ray detected value after preparation to the clipping unit 8 after the preparation unit makes various preparation such as offset correction normally performed.

The clipping unit 8 is provided with a function for receiving the X-ray detected value from the X-ray detector 3 via DAS 4, the data transmission equipment 5 and the preparation unit 7 and executing clipping.

The output correction unit 9 is provided with a function for applying a mean value maintenance correction process to the X-ray detected value after clipping so that the separation of local means of the X-ray detected values before and after clipping is reduced. If only the X-ray detected value which is an object of the mean value maintenance correction process is at least data before and after clipping, it may be also any data before and after preparation and other required processing. Therefore, data before and after preparation and other required processing which can be regarded as the X-ray detected value will be called an X-ray detected value below.

The output correction unit 9 is provided with a function for creating bins by binning the X-ray detected value for example to acquire the local means of the X-ray detected values before and after clipping and acquiring the sum or the mean value of X-ray detected values in each bin.

The clipping-correction unit 14 is provided with a function for applying the clipping process to the X-ray detected value and applying the mean value maintenance correction process to the X-ray detected value so that the separation of the local means of the X-ray detected values before and after clipping is reduced by the clipping unit 8 and the output correction unit 9.

The reclipping unit 10 is provided with a function for applying a reclipping process to the X-ray detected value after the mean value maintenance correction process received from the output correction unit 9.

The logarithmic transformation unit 11 is provided with a function for generating projection data by applying a logarithmic transformation process and various processes normally performed to the X-ray detected value after reclipping received from the reclipping unit 10 and a function for writing the generated projection data to the storage unit 13.

The image reconfiguration unit 12 is provided with a function for reading the projection data stored in the storage unit 13 and generating an X-ray CT image by applying required preparation and an image reconfiguration process and a function for sending the X-ray CT image to a display device not shown and instructing the display device to display it.

Next, the action of the radiological image diagnostic system 1 will be described.

Figure 2:
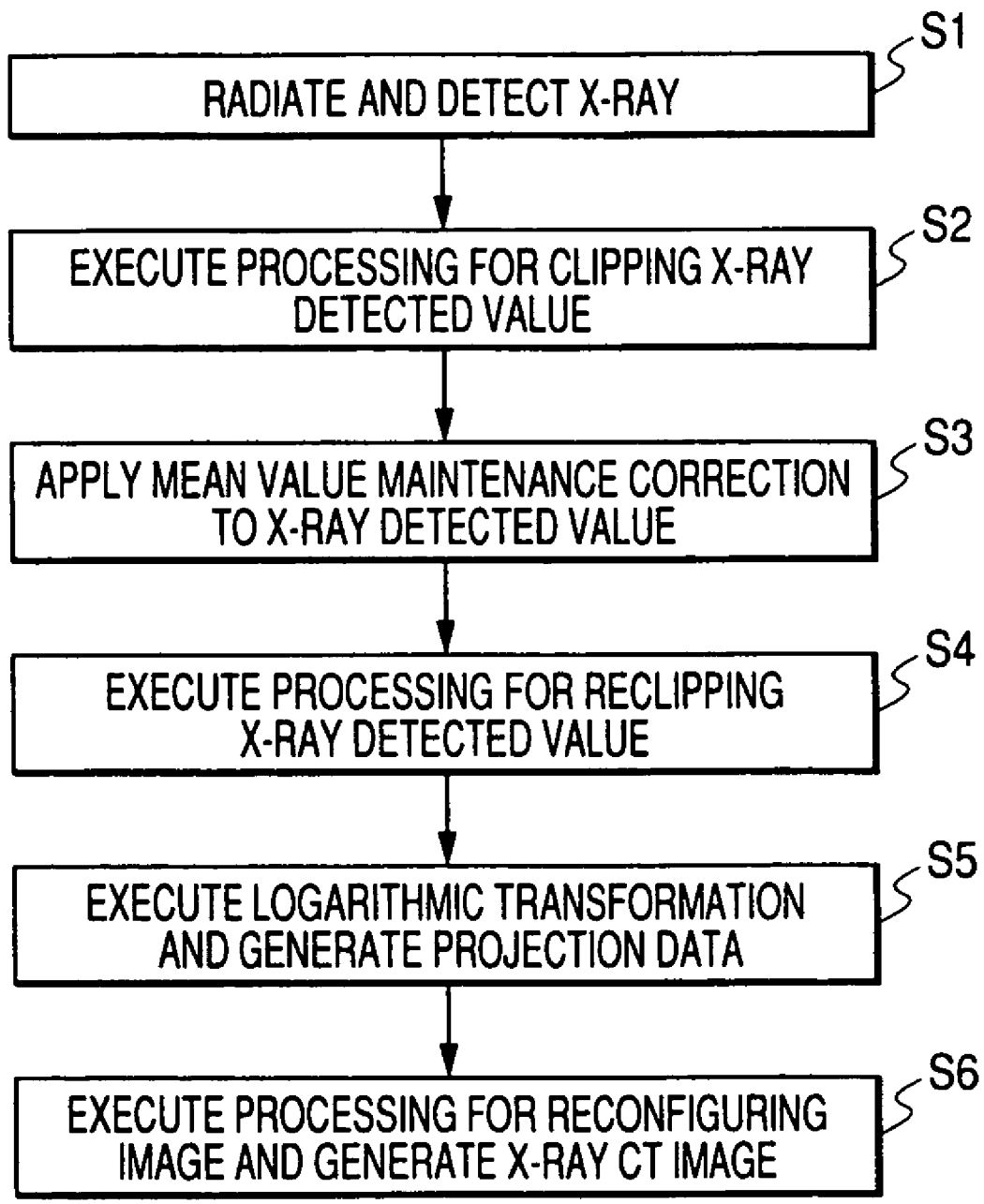
FIG. 2 is a flowchart showing a procedure when an X-ray CT image is reconfigured by the radiological image diagnostic system shown in FIG. 1.

FIG. 2 is a flowchart showing a procedure when the X-ray CT image is reconfigured by the radiological image diagnostic system 1 shown in FIG. 1 and a code in which a numeral is added to S denotes each step of the flowchart.

First, in a step S1, X-rays are radiated on the examined body P from the X-ray tube 2 and are detected in the X-ray detector 3. The X-ray detector 3 sends the detected X-ray dosage to the preparation unit 7 via DAS 4 and the data transmission equipment 5 as an X-ray detected value. The preparation unit 7 sends the X-ray detected value to the clipping unit 8 and the output correction unit 9 after the preparation unit applies various preparation to the X-ray detected value.

Next, in a step S2, the clipping unit 8 applies the clipping process to the X-ray detected value received from the X-ray detector 3 via DAS 4, the data transmission equipment 5 and the preparation unit 7.

That is, as shown in an expression (1), the X-ray detected value in each view i and each lay j shall be $x_{i,j}$, in case the X-ray detected value $x_{i,j}$ is equal to or smaller than 1, an X-ray detected value $x'_{i,j}$ after clipping shall be 1, and in the meantime, in case the X-ray detected value $x_{i,j}$ is equal to or larger than 1, the X-ray detected value $x'_{i,j}$ after clipping shall be the X-ray detected value $x_{i,j}$ before clipping as it is.

$$x'_{i,j} = \begin{cases} 1 & \text{if } x_{i,j} \leq 1 \\ x_{i,j} & \text{else} \end{cases} \quad (1)$$

The clipping unit 8 sends the X-ray detected value $x'_{i,j}$ after clipping to the output correction unit 9.

Next, in a step S3, the output correction unit 9 applies the mean value maintenance correction process to the X-ray detected value $x'_{i,j}$ after clipping so that a separation between the local mean of the X-ray detected value $x'_{i,j}$ after clipping and the local mean of the X-ray detected value $x_{i,j}$ before clipping is reduced.

For it, the output correction unit 9 first bins the X-ray detected value $x_{i,j}$ before clipping received from the X-ray detector 3 via DAS 4, the data transmission equipment 5 and the preparation unit 7 and the X-ray detected value $x'_{i,j}$ after clipping received from the clipping unit 8 in each small group and calculates the sum of the X-ray detected values $x_{i,j}$, $x'_{i,j}$ in acquired each bin $X_{I,J}$, $X'_{I,J}$.

That is, when the size in a direction of the view of the binned small groups is M, the size in a direction of the lay is N and { } is a symbol showing a numerical array, the output correction unit 9 generates the bin $X_{I,J}$ acquired by an expression (2) by binning the X-ray detected value $x_{i,j}$ before clipping.

$$X_{I,J} = \{x_{IM+m, JN+n}\} \quad (2)$$

However, "m and n" are an integer and $$m = -(M-1)/2 \sim (M-1)/2, \; n = -(N-1)/2 \sim (N-1)/2.$$

Further, the output correction unit 9 calculates the sum S of the whole X-ray detected values $x_{IM+m, JN+n}$ before clipping which are components in the bin $X_{I,J}$ every bin $X_{I,J}$ according to an expression (3).

$$S = \sum_m \sum_n x_{IM+m, JN+n} \quad (3)$$

Similarly, the output correction unit 9 generates a bin $X'_{I,J}$ acquired in an expression (4) acquired by binning the X-ray detected value $x'_{i,j}$ after clipping.

$$X'_{I,J} = \{x'_{IM+m, JN+n}\} \quad (4)$$

Further, the output correction unit 9 calculates the sum S' of the whole X-ray detected values $x'_{IM+m, JN+n}$ after clipping which are components in the bin $X'_{I,J}$ every bin $X'_{I,J}$ according to an expression (5).

$$S' = \sum_m \sum_n x'_{IM+m, JN+n} \quad (5)$$

Next, the output correction unit 9 calculates the number R of the X-ray detected values $x'_{IM+m, JN+n}$ ($x'_{IM+m, JN+n} \neq$) not clipped of the X-ray detected values $x'_{IM+m, JN+n}$ in the bin $X'_{I,J}$ after clipping.

The output correction unit 9 corrects the X-ray detected values $x'_{IM+m, JN+n}$ by uniformly adding a raised amount in the bin $X'_{I,J}$ by clipping to each X-ray detected value $x'_{IM+m, JN+n}$ ($x'_{IM+m, JN+n} \neq$) not clipped according to an expression (6-1) for example and acquires corrected X-ray detected values $x''_{IM+m, JN+n}$.

As a result, a new bin $X''_{I,J}$ shown in the expression (6-1) is generated.

$$x''_{IM+m,JN+n} = \begin{cases} 1 & \text{if } x'_{IM+m,JN+n} = 1 \\ x'_{IM+m,JN+n} + \dfrac{(S-S')}{R} & \text{else} \end{cases} \quad (6\text{-}1)$$

$$X''_{I,J} = \{x''_{IM+m,JN+n}\} \quad (6\text{-}2)$$

The mean value of the X-ray detected values $x''_{IM+m, JN+n}$ generated as described above in the bin $X''_{I,J}$ after mean value maintenance correction is recovered so that the mean value is equal to the mean value of the X-ray detected values $x_{IM+m, JN+n}$ in the bin $X_{I,J}$ before clipping.

Figure 3:
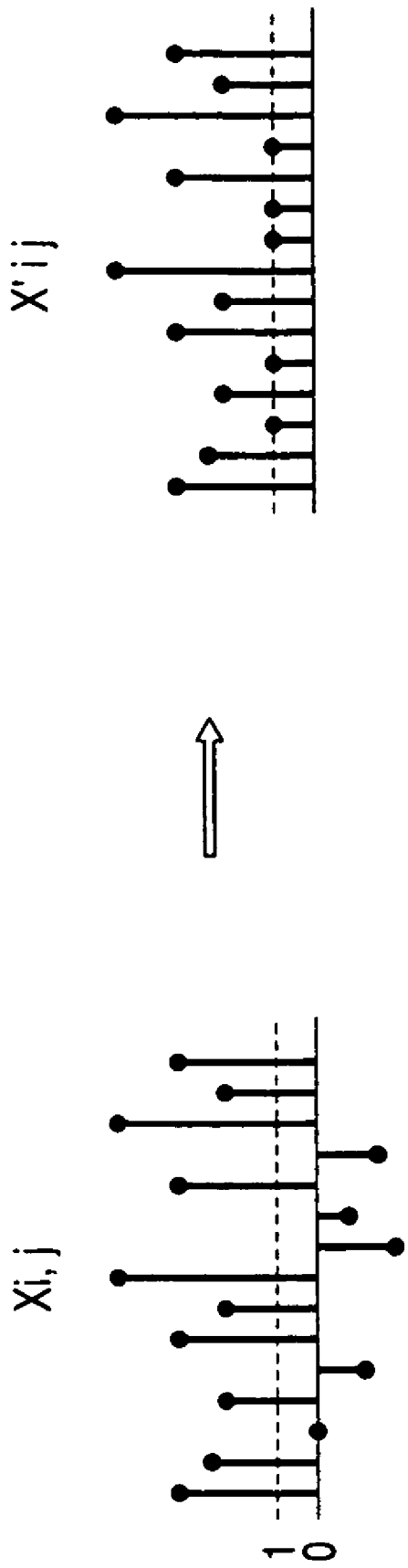
FIG. 3 show a procedure for processing an X-ray detected value by a conventional type radiological image diagnostic system.
Figure 4:
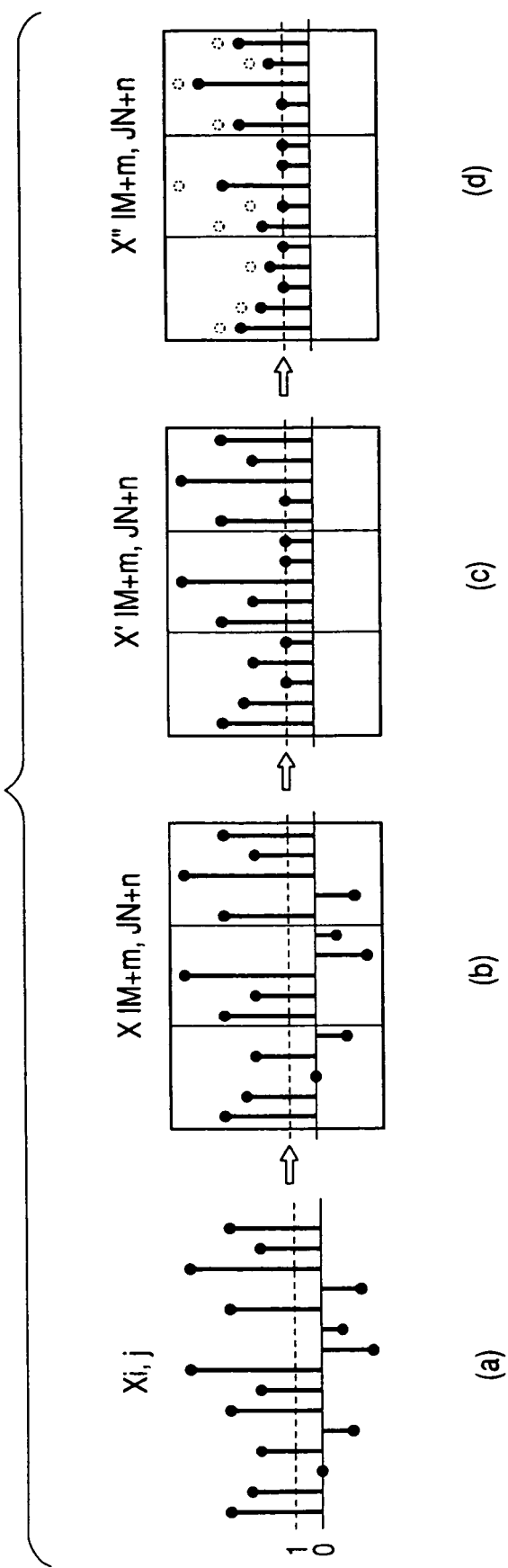
FIG. 4 show a procedure for processing an X-ray detected value by the radiological image diagnostic system shown in FIG. 1.

FIG. 3 shows a procedure of processing applied to an X-ray detected value by the conventional type radiological image diagnostic system and FIG. 4 shows a procedure of processing applied to the X-ray detected value by the radiological image diagnostic system 1 shown in FIG. 1.

The generated bins $X_{I,J}$, $X'_{I,J}$, $X''_{I,J}$ are two-dimensional including the view i and the lay j, however, they may be also one-dimensional. Then, the bins $X_{I,J}$, $X'_{I,J}$, $X''_{I,J}$ will be described as one-dimensional below.

The X-ray detected value $x_{i,j}$ output from the X-ray detector 3 has dispersion as shown in FIG. 3A and FIG. 4A and includes data the value of which is smaller than 1. As only clipping is applied in the conventional type radiological image diagnostic system, the X-ray detected value data $x'_{i,j}$ is acquired by raising a part smaller than 1 of the X-ray detected value to 1 as shown in FIG. 3B.

In the meantime, in the radiological image diagnostic system 1 shown in FIG. 1, the X-ray detected value $x_{i,j}$ output from the X-ray detector 3 is binned to be divided into small groups of five pieces of data for example and the bin $X_{I,J}$ is generated as shown in FIG. 4B. At this time, the sum (or the mean value) of the X-ray detected values $x_{IM+m, JN+n}$ in the bin $X_{I,J}$ is calculated.

The clipping process is applied to the X-ray detected values $x_{IM+m, JN+n}$ included in each bin $X_{I,J}$ and the X-ray detected value data $x'_{IM+m, JN+n}$ after clipping shown in FIG. 4C is acquired. The mean value of the X-ray detected value data $x'_{IM+m, JN+n}$ in the bin $X'_{I,J}$ after clipping is shifted from the mean value of the X-ray detected value data $x_{IM+m, JN+n}$ in the bin $X_{I,J}$ before clipping.

Then, a mean value maintenance correction process in the bin $X'_{I,J}$ is applied to the X-ray detected values $x'_{IM+m, JN+n}$ after clipping, the X-ray detected values $x''_{IM+m, JN+n}$ shown by a full line in FIG. 4D are acquired, the mean value in each bin $X''_{I,J}$ is maintained. That is, the X-ray detected values $x'_{IM+m, JN+n}$ not clipped of the X-ray detected values $x'_{IM+m, JN+n}$ in the bin $X'_{I,J}$ after clipping are corrected and the mean value is maintained.

The X-ray detected values $x''_{IM+m, JN+n}$ in the bin $X''_{I,J}$ after mean value maintenance correction may be a negative value or a value smaller than 1. Therefore, logarithmic transformation cannot be applied to the X-ray detected values $x''_{IM+m, JN+n}$ in the bin $X''_{I,J}$ after mean value maintenance correction as they are.

Then, the output correction unit 9 sends the X-ray detected values $x''_{IM+m, JN+n}$ in the bin $X''_{I,J}$ after mean value maintenance correction to the reclipping unit 10.

In a step S4, the reclipping unit 10 acquires X-ray detected values $x'''_{IM+m, JN+n}$ after reclipping by applying the clipping process to the X-ray detected values $x''_{IM+m, JN+n}$ in the bin $X''_{I,J}$ after mean value maintenance correction received from the output correction unit 9 again according to an expression (7-1). As a result, a bin $X'''_{I,J}$ after reclipping shown in an expression (7-2) is generated.

$$x'''_{IM+m,JN+n} = \begin{cases} 1 & \text{if } x''_{IM+m,JN+n} \le 1 \\ x''_{IM+m,JN+n} & \text{else} \end{cases} \quad (7\text{-}1)$$

$$X'''_{I,J} = \{x'''_{IM+m,JN+n}\} \quad (7\text{-}2)$$

The mean value of the X-ray detected values $x''_{IM+m, JN+n}$ in the bin $X''_{I,J}$ after mean value maintenance correction is recovered so that the mean value is equal to the mean value of the X-ray detected values $x_{IM+m, JN+n}$ in the bin $X_{I,J}$ before clipping, however, the mean of the X-ray detected values $x'''_{IM+m, JN+n}$ in the bin $X'''_{I,J}$ after reclipping is statistically slightly larger than the mean value of the X-ray detected values $x_{IM+m, JN+n}$ in the bin $X_{I,J}$ before clipping.

Generally, the rise is insignificant and the result of mean value maintenance correction is sufficiently satisfactory, however, if the same process is applied again, the further satisfactory result may be acquired. Then, the raised amount of the mean value may be also reduced by instructing the reclipping unit 10 to send the X-ray detected values $x'''_{IM+m, JN+n}$ after reclipping to the output correction unit 9 and to apply the similar processes to those in the step S3 and the step S4 again. Normally, if the similar process is twice repeated, the raised amount of the mean value can be sufficiently reduced.

The reclipping unit 10 sends the X-ray detected values $x'''_{IM+m, JN+n}$ in the bin $X'''_{I,J}$ after reclipping to the logarithmic transformation unit 11.

Next, in a step S5, the logarithmic transformation unit 11 generates projection data by applying the logarithmic transformation process and various processing to the X-ray detected values $x'''_{IM+m, JN+n}$ in the bin $X'''_{I,J}$ after reclipping received from the reclipping unit 10.

The logarithmic transformation unit 11 writes the projection data to the storage unit 13.

At this time, if necessary, a process such as a process for reducing a streak artifact in an ultralow dosage area of the X-ray detected value is suitably executed.

Next, in a step S6, the image reconfiguration unit 12 generates an X-ray CT image by reading the projection data stored in the storage unit 13 and applying required preparation and an image reconfiguration process.

Figure 5:
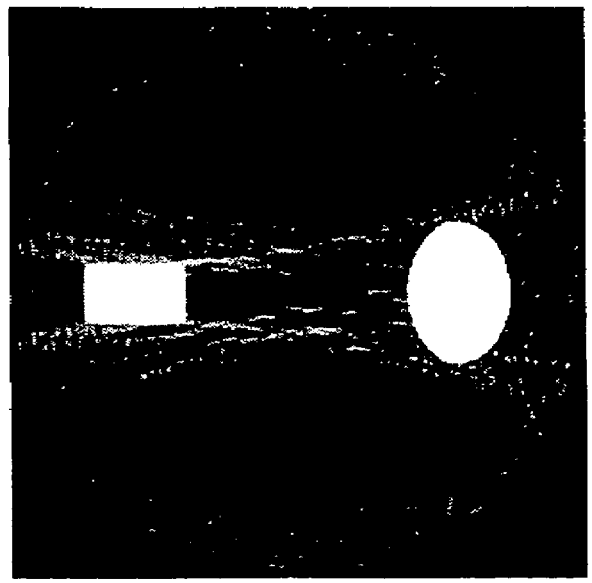
FIG. 5 shows an X-ray CT image photographed by the conventional type radiological image diagnostic system.
Figure 6:
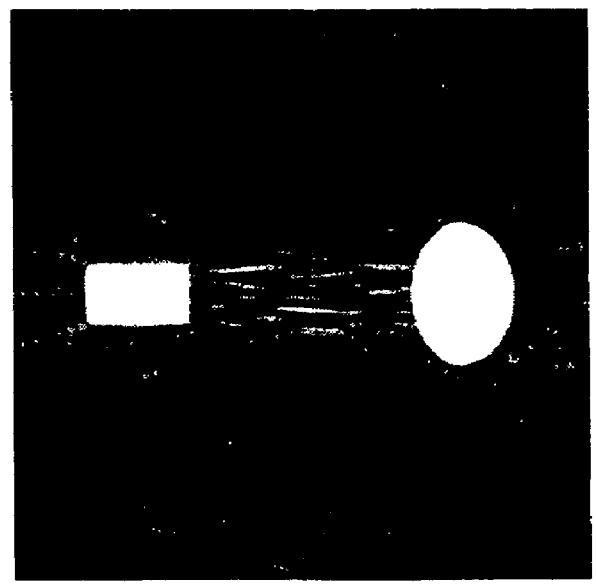
FIG. 6 shows an X-ray CT image photographed by the radiological image diagnostic system shown in FIG. 1.

FIG. 5 shows an X-ray CT image photographed by the conventional type radiological image diagnostic system and FIG. 6 shows an X-ray CT image photographed by the radiological image diagnostic system 1 shown in FIG. 1. However, a process for reducing a streak artifact made by noise is separately applied to the X-ray CT images shown in FIGS. 5 and 6.

As clear from FIG. 5, upper and lower black ellipses denote air, left and right white rectangle and ellipse denote a substance equivalent to a bone the CT value of which is high, however, X-ray attenuation is fierce in a lateral X-ray path that passes the white rectangle and ellipse, clipping occurs, a CT value is low in a central area, and a dark zone occurs.

In the meantime, in FIG. 6, it can be verified that the dark zone by clipping which occurs in the conventional type is substantially eliminated.

According to the radiological image diagnostic system 1 described above, as a shifted amount by clipping of the mean value of the projection data is reduced, the shift of a CT value in the X-ray CT image and the occurrence of shading can be reduced.

The output correction unit 9 uniformly subtracts a fixed value from the X-ray detected value data not clipped in the bin and applies the mean value maintenance correction process so that the mean value of the X-ray detected values in the bin before and after clipping is equal, however, the mean value of the X-ray detected values in the bin before and after clipping may be also not necessarily uniform and may be also in a fixed range.

For example, a subtracted amount may be also adjusted according to a value of X-ray detected value data not clipped in the bin. For its concrete example, the larger the X-ray detected value is, the larger value is subtracted, in case a value of X-ray detected value data not clipped is small, a light value is subtracted, in case for a subtracted amount, the result of subtraction is equal to or extracts 1, a second clipping process is not required, and sufficient mean value recovery effect can be practically acquired without a second mean value maintenance process.

Figure 7:
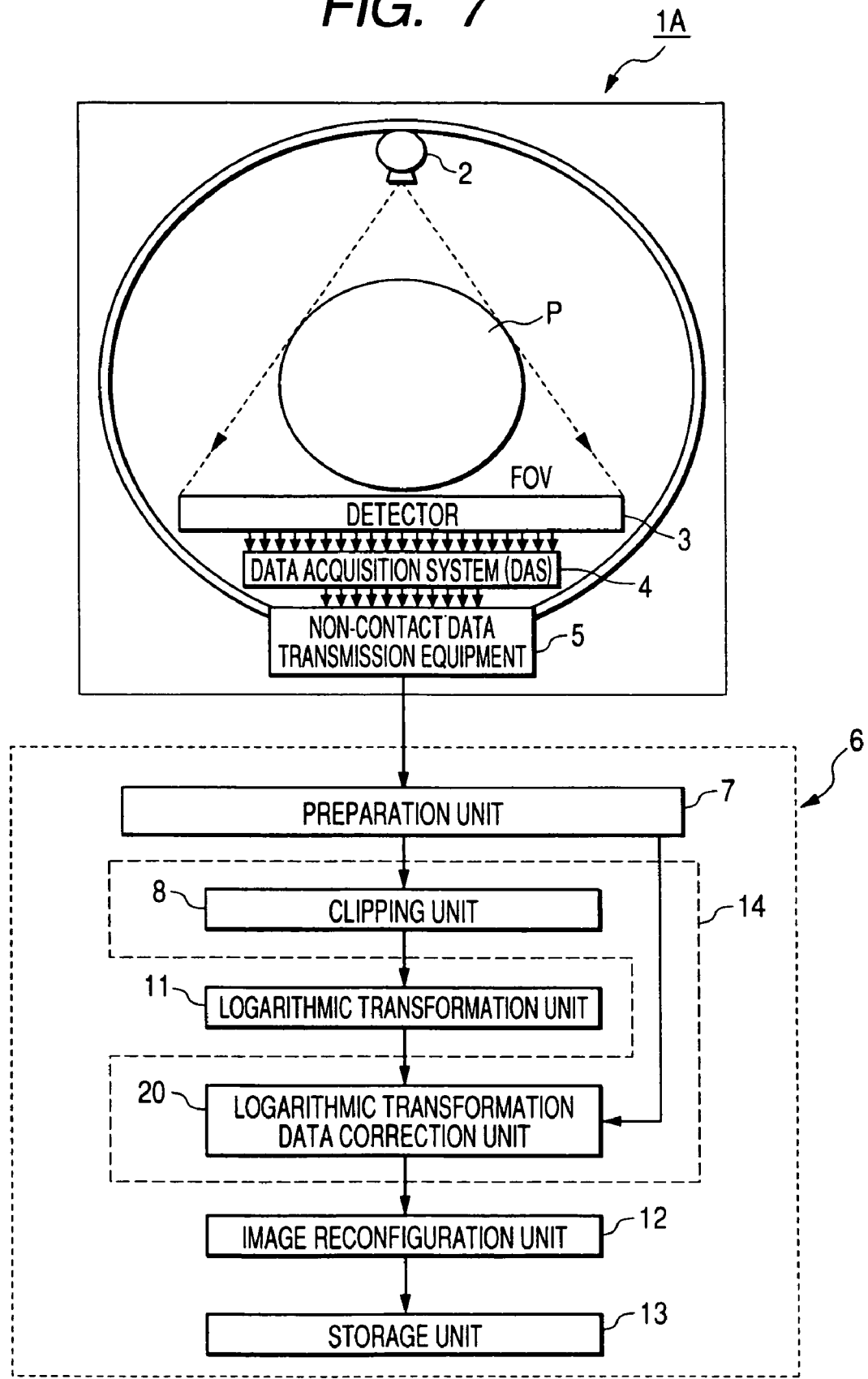
FIG. 7 is a block diagram showing a second embodiment of the radiological image diagnostic system according to the invention.

FIG. 7 is a block diagram showing a second embodiment of the radiological image diagnostic system according to the invention.

In a radiological image diagnostic system 1A shown in FIG. 7, the function of a controller 6 is different from that in the radiological image diagnostic system 1 shown in FIG. 1. As the other configuration and action are substantially similar to those in the radiological image diagnostic system 1 shown in FIG. 1, the same reference numeral is allocated to the same configuration and its description is omitted.

The controller 6 of the radiological image diagnostic system 1A functions as a preparation unit 7, a clipping unit 8, a logarithmic transformation unit 11, a logarithmic transformation data correction unit 20 and an image reconfiguration unit 12 and further, is provided with a storage unit 13. A clipping-correction unit 14 is realized by the clipping unit 8 and the logarithmic transformation data correction unit 20.

The clipping unit 8 is provided with a function for receiving an X-ray detected value from an X-ray detector 3 via DAS 4, data transmission equipment S and the preparation unit 7 and applying a clipping process.

The logarithmic transformation unit 11 is provided with a function for generating logarithmic transformation data by a logarithmic transformation process based upon the X-ray detected value after clipping received from the clipping unit 8. If only the logarithmic transformation data is data that can be regarded as substantially similar to data acquired by applying the logarithmic transformation process to the X-ray detected value, it maybe also data acquired by another process. Therefore, the logarithmic transformation data is projection data or data in an intermediate process on the way to projection data.

The logarithmic transformation data correction unit 20 is provided with a function for receiving the logarithmic transformation data and executing a mean value correction process for multiplying by a coefficient so that the local mean approaches a value generated by logarithmic transformation from the local mean of the X-ray detected values before clipping. The logarithmic transformation data correction unit 20 is provided with a function for generating bins by binning the logarithmic transformation data and the X-ray detected value for example so as to acquire the local mean of the logarithmic transformation data and the X-ray detected value before clipping and calculating the mean in the bin.

The clipping-correction unit 14 is provided with a function for applying the clipping process to the X-ray detected value and applying the mean value correction process to the logarithmic transformation data so that a separation between the local mean of the logarithmic transformation data after clipping and a value equivalent to the logarithmic transformation data and generated by logarithmic transformation based upon the local mean of the X-ray detected values before clipping is reduced by clipping unit 8 and the logarithmic transformation data correction unit 20.

The image reconfiguration unit 12 is provided with a function for generating an X-ray CT image by applying required preparation and an image reconfiguration process to logarithmic transformation data corrected by the logarithmic transformation data correction unit 20.

Next, the action of the radiological image diagnostic system 1A will be described.

Figure 8:
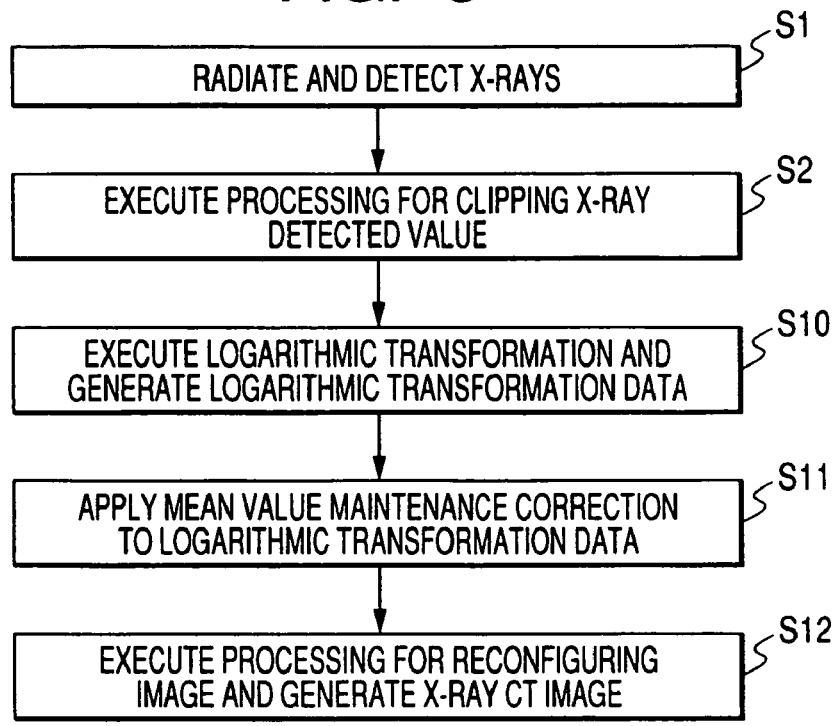
FIG. 8 is a flowchart showing a procedure when an X-ray CT image is reconfigured by the radiological image diagnostic system shown in FIG. 7.
Figure 9:
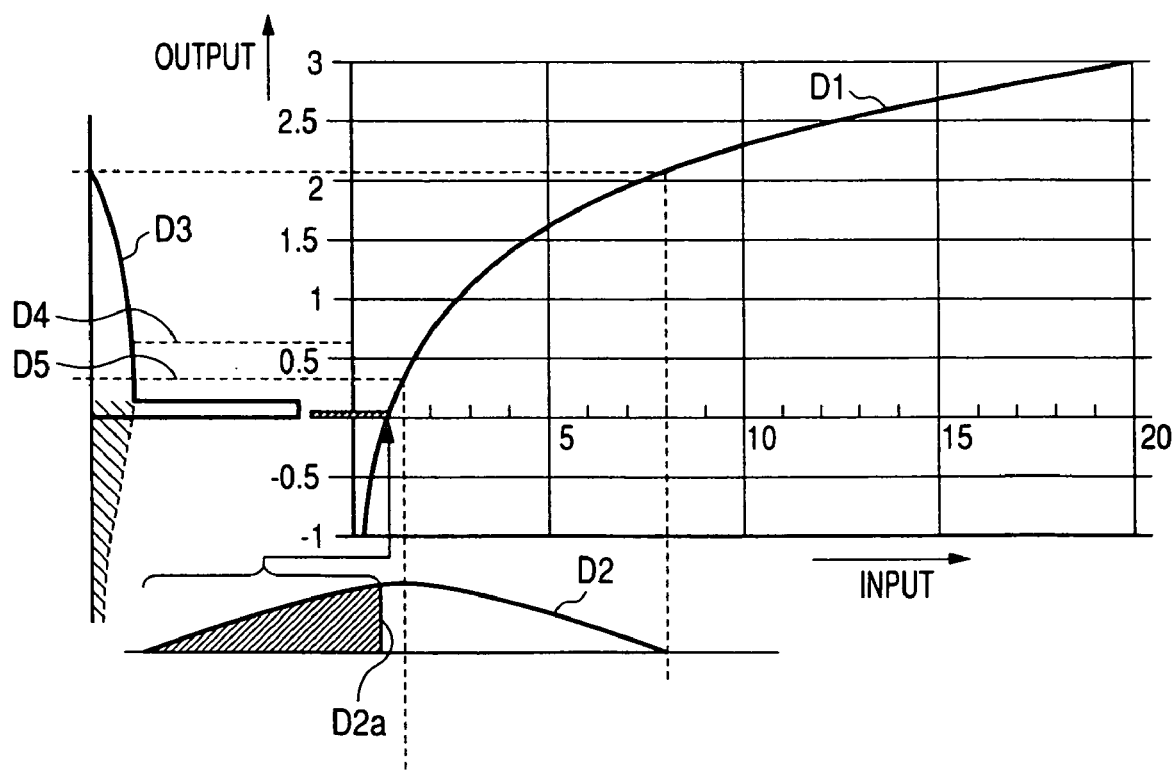
FIG. 9 is an explanatory drawing for explaining a concept of clipping that occurs in case an X-ray detected value is in an ultralow dosage area.

FIG. 8 is a flowchart showing a procedure when an X-ray CT image is reconfigured by the radiological image diagnostic system 1A shown in FIG. 7 and a code in which a numerical is added to S denotes each step of the flowchart. The same reference numeral is allocated to the similar step to that in FIG. 2.

First, in a step S1, X-rays are radiated on an examined body P from an X-ray tube 2 and an X-ray detected value acquired by the X-ray detector 3 and DAS 4 is sent to the clipping unit 8 via the data transmission equipment 5 and the preparation unit 7.

Next, in a step S2, the clipping unit 8 applies a clipping process to the X-ray detected value received from the X-ray detector 3 via DAS 4, the data transmission equipment 5 and the preparation unit 7. The clipping unit 8 sends the X-ray detected value after clipping to the logarithmic transformation unit 11.

Next, in a step S10, the logarithmic transformation unit 11 generates logarithmic transformation data by applying a logarithmic transformation process and various processes to the X-ray detected value after clipping received from the clipping unit 8.

Next, in a step S11, the logarithmic transformation data correction unit 20 receives the logarithmic transformation data from the logarithmic transformation unit 11 and corrects the logarithmic transformation data so that the mean value of the logarithmic transformation data approaches logarithmic transformation data acquired by logarithmic transformation from the mean value of the X-ray detected values before clipping.

Therefore, the logarithmic transformation data correction unit 20 bins the logarithmic transformation data. Next, the logarithmic transformation data correction unit 20 acquires a coefficient Z for correcting logarithmic transformation data in each bin based upon an X-ray detected value $x_n$ before clipping, an X-ray detected value $x'_n$ after clipping and the number of data N in binned each bin according to an expression (8). However, in the expression, a one-dimensional case is shown.

For the process, the mean in the bin of the X-ray detected values before clipping and its logarithmic transformation value are required, the logarithmic transformation data correction unit 20 accesses to the X-ray detected value before clipping, bins it, and calculates a logarithmic transformation value of the mean in the bin. Or for the same object, the logarithmic transformation data correction unit 20 instructs the clipping unit 8 to output the mean in the bin of the X-ray detected value before clipping by predetermined binning, instructs the logarithmic transformation unit 14 to apply logarithmic transformation to the mean in the bin, and may also receive the logarithmic transformation value.

$$Z \cdot \sum_{n=1}^{N} \log(x'_n) = \log\left(\frac{\sum_{n=1}^{N} x_n}{N}\right) \tag{8}$$

The logarithmic transformation data correction unit 20 corrects logarithmic transformation data by multiplying logarithmic transformation data in each bin by the acquired coefficient Z.

As logarithmic transformation data generated based upon the X-ray detected value $x'_n$ the value of which is changed to 1 by clipping is log(1)=0, the value is unchanged even if it is multiplied by the coefficient Z. Therefore, if the logarithmic transformation data is multiplied by the coefficient Z once and is corrected, the mean value of the logarithmic transformation data after correction is equal to the mean value of logarithmic transformation data acquired based upon the X-ray detected value before clipping. There is no guarantee that both are completely coincident depending upon a unit in which a numeric value dealt by the system is quantized, that is, a round-up/round-down error and the limitation of a maximum dealt numeric value range, however, both practically have sufficient close values.

The logarithmic transformation data correction unit 20 sends logarithmic transformation data after correction to the image reconfiguration unit 12.

Next, in a step S12, the image reconfiguration unit 12 receives the logarithmic transformation data after correction from the logarithmic transformation data correction unit 20, makes required preparation to be projection data, and generates an X-ray CT image by applying an image reconfiguration process to the projection data. As a result, the image reconfiguration unit can acquire the X-ray CT image in which a shifted amount of the mean value of the logarithmic transformation data by clipping is reduced. The generated projection data and images are stored in the storage unit 13.

That is, the radiological image diagnostic system 1 shown in FIG. 1 executes the mean value maintenance correction process of the X-ray detected value after clipping before the logarithmic transformation of the X-ray detected value, while the radiological image diagnostic system 1A multiplies by the coefficient of logarithmic transformation data so that the mean value in the bin of the logarithmic transformation data after logarithmic transformation is equal to logarithmic transformation data acquired based upon the mean value of the X-ray detected values before clipping or has a closer value and corrects.

As described above, according to the radiological image diagnostic system 1A, in addition to the similar effect to that of the radiological image diagnostic system 1 shown in FIG. 1, as a mean value maintenance correction process is not required to be repeatedly executed to enhance the precision, calculation can be facilitated.

Data which is an object of mean value maintenance correction by the radiological image diagnostic system 1A will be supplemented below. In above description, logarithmic transformation data, that is, a value immediately after logarithmic transformation is corrected. However, as long as the X-ray detected value before clipping or the local mean is known, data acquired by further executing processes since logarithmic transformation data, for example, projection data can be also corrected. That is, if the local mean of the X-ray detected values before clipping is attached from logarithmic transformation to a later arbitrary process, its output value is a desired value as the local mean of data acquired by attaching clipped data to the process. As long as the contents of processing up to the process are definite, a correction expression equivalent to the expression (8) can be configured in view of the contents. In case many contents are reflected, a correction expression is intricate, however, in principle, it is known that a process for correcting the local mean can be applied to data at any stage.

To sum up, in the radiological image diagnostic system 1 shown in FIG. 1, the clipping-correction unit 14 is realized by the clipping unit 8 and the output correction unit 9 and the process for correcting the local mean is applied to the X-ray detected value, however, in the meantime, in the radiological image diagnostic system 1A shown in FIG. 7, the clipping-correction unit 14 is realized by the clipping unit 8 and the logarithmic transformation data correction unit 20, and the process for correcting the local mean is applied to logarithmic transformation data.

As described above, an object for correcting the local mean by the clipping-correction unit 14 can be arbitrary data having predetermined relation with the X-ray detected value independent of before and after logarithmic transformation.

In case preparation required for correcting the local mean of data is made prior to the clipping process, the process for correcting the local mean of data is not necessarily executed after clipping, and the clipping process and the process for correcting the local mean of data may be also executed together without definitely discriminating them.

Next, a transformed example of mean value maintenance correction by the radiological image diagnostic systems 1, 1A equivalent to each embodiment will be described.

In the case of mean value maintenance correction by the radiological image diagnostic systems 1, 1A equivalent to each embodiment, the binning of X-ray detected value data is executed to acquire the local mean of the X-ray detected values before clipping, however, a local mean value can be also acquired not by binning but by smoothing. That is, a smoothing process is executed in directions of a view i and a lay j for the whole area or a part of an X-ray detected value (A) before clipping and the result of the smoothing process (B) shows the distribution of the local mean of the X-ray detected values. For the data, as a result of smoothing, most of abnormal values smaller than 1 are turned to 1 or a larger number. Even if the data is attached to clipping, further logarithmic transformation or a further later process, a problem of clipping scarcely has an effect upon the result (C). However, dimness is included because of smoothing. In the meantime, X-ray detected value data to which no smoothing is applied is attached to clipping, further logarithmic transformation or a further later process as usual, however, though a problem of clipping will have an effect upon the output (D), dimness is not included. D is further smoothed using the same filter as a filter used for smoothing A, however, the output is E. Clipping has an effect upon the local mean of E and dimness is similar to that in C. In an area in which clipping occurs in D, "F" the local mean of which is close to C is desired and is acquired by the following expression (9).

$$F_{i,j} = (1-W) \times D_{i,j} + W \times C_{i,j} \tag{9}$$

W=1 if $B_{i,j} \leq 0$

W=−1/X if $0 \leq B_{i,j} < X$

W=0 if $X \leq B_{i,j}$

X denotes a threshold value and W denotes a weight function. That is, in case the local mean of X-ray detected values before clipping is smaller than X, the smaller the local mean is, the closer to C F is, and as a problem of clipping does not occur if the local mean of X-ray detected values before clipping is a sufficiently large value, a value of D is adopted as F as it is. The setting of X is arbitrary, however, it is desirable that X has the similar value to the standard deviation of the amplitude of noise included in an X-ray detected value. For a value to be referred to determine W, A may be also used in place of B, however, in this case, for X, a value sufficiently larger than 1 should be selected.

Owing to F hereby acquired, a problem of clipping is greatly relaxed and in a situation in which no clipping occurs, no dimness is caused.

When F is acquired as described above, normal processing afterward has only to be executed using F. In case F is projection data, an image has only to be reconfigured and in case F is data immediately after clipping, an image is reconfigured as projection data via logarithmic transformation and other processing. In case F is a value immediately after logarithmic transformation, projection data is acquired by later processing and an image is reconfigured.

As described above, projection data in which a shifted amount of a mean value by clipping is reduced can be acquired and an X-ray CT image in which the shift of a CT value and shading are relaxed can be reconfigured.

That is, independent of whether binning or smoothing is used, a mean value maintenance correction process has only to be executed so that the local mean value B (i, j) of X-ray detected values before clipping is grasped and the local mean value P (i, j) of projection data is close to projection data generated based upon the local mean value B (i, j) of the X-ray detected values before clipping.

Finally, the following will be supplemented. It is described above that clipping is means for fixing input equal to or smaller than 1 to 1 and executing logarithmic transformation. However, even if a clipped level is not 1 but another numeric value, it is clear that the invention similarly has effectiveness.

Not a clipping method of uniformly clipping an input value equal to or smaller than a clipped level to be the clipped level but clipping of varying an inconvenient input value for processing for the system according to a function except uniformity and turning it to a convenient value is possible.

For example, in a method called a log-tweak described in a document, "Method for Suppressing Streak Artifacts in CT Resulting from Excessive Noise" on pp. 272 to 276 of Medical Imaging Technology, 21 (4), 2003 written by I. Mori and M. Kazama, when an X-ray detected value is a very small value, processing is executed using not a logarithmic function but a linear function, however, this is equivalent to raising an input value using a certain function and executing logarithmic transformation, and as in the above-mentioned clipping method, this can be regarded as varying an inconvenient input value for logarithmic transformation so that it is convenient.

In such a case, the shift of the local mean is also caused, however, as to it, the methods described in the invention are effective. That is, clipping in the invention means the whole processing for varying an inconvenient input value for processing for the system using a function except uniformity and turning it to a convenient value and the invention has universality as a method of bringing the local mean of projection data generated by clipping close to a right value in case an X-ray detected value is very small.

What is claimed is:

1. An X-ray CT system, comprising:
a radiation generating unit which generates a radiation;
a radiation detecting unit which detects the radiation from the radiation generating unit;
a clipping-correction unit which applies a clipping process to a radiation detected value by the radiation detecting unit and applies a mean value correction process to data acquired based upon the radiation detected value so that the separation of the local mean of the data acquired based upon the radiation detected value before and after the clipping process is reduced, the radiation detected value being data before image reconstruction for generating an X-ray CT image;
an image reconfiguration unit which generates an image using data acquired based upon the radiation detected value after the clipping process and after the mean value correction process; a reclipping unit which applies a further clipping process to a radiation detected value after applying the mean value maintenance correction process; and a logarithmic transformation unit which generates projection data by applying a process including a logarithmic transformation process to the radiation detected value after the reclipping process.

2. An X-ray CT system according to claim 1, wherein:
the local mean is calculated based upon a mean value in a bin generated by binning.

3. An X-ray CT system according to claim 1, wherein:
the local mean is calculated by a smoothing process.

4. An X-ray CT system, comprising:
a radiation generating unit which generates a radiation;
a radiation detecting unit which detects the radiation from the radiation generating unit;
a clipping unit which applies a clipping process to a radiation detected value by the radiation detecting unit, the radiation detected value being data before image reconstruction for generating an X-ray CT image;
an output correction unit which applies a mean value maintenance correction process to a radiation detected value after the clipping process so that the separation of the local mean of the radiation detected values before and after clipping is reduced;
a logarithmic transformation unit which generates projection data by applying a process including a logarithmic transformation process to a radiation detected value after the mean value maintenance correction process; a reclipping unit which applies a further clipping process to a radiation detected value after applying the mean value maintenance correction process, wherein the logarithmic transformation unit generates projection data by applying a process including a logarithmic transformation process to the radiation detected value after the reclipping process.

5. A data processing method of an X-ray CT system, comprising:
a step of applying a clipping process to a radiation detected value and applying a mean value correction process to data acquired based upon the radiation detected value so that the separation of the local mean of the data acquired based upon the radiation detected value before and after clipping is reduced, the radiation detected value being data before image reconstruction for generating an X-ray CT image; and
a step of generating an image using data acquired based upon a radiation detected value after the clipping process and after the mean value correction process; a step of applying a reclipping process to the radiation detected value after the mean value maintenance correction process; and a step of generating projection data by applying a process including a logarithmic transformation process to a radiation detected value after the reclipping process.

6. A data processing method of an X-ray CT system according to claim 5, wherein:
the mean value correction process is a mean value maintenance correction process applied to the radiation detected value after the clipping process.

7. A data processing method of an X-ray CT system according to claim 5, wherein:
the mean value correction process is a mean value correction process which multiplies by a coefficient so that the local mean of the logarithmic transformation data approaches a value generated by logarithmic transformation based upon the local mean of the radiation detected value before clipping.

* * * * *